(12) United States Patent
Baldino et al.

(10) Patent No.: US 6,452,050 B1
(45) Date of Patent: Sep. 17, 2002

(54) SYNTHESIS AND USE OF α-KETOAMIDE DERIVATIVES AND ARRAYS

(75) Inventors: Carmen M. Baldino, Lexington; David L. Coffen, Cambridge; Stewart D. Chipman, Reading; Hong Cheng, Brighton, all of MA (US)

(73) Assignee: ArQule, Inc., Woburn, MA (US)

( * ) Notice: Subject to any disclaimer, the term of this patent is extended or adjusted under 35 U.S.C. 154(b) by 0 days.

(21) Appl. No.: 09/531,737

(22) Filed: Mar. 21, 2000

Related U.S. Application Data

(63) Continuation of application No. 09/061,752, filed on Apr. 16, 1998, now Pat. No. 6,143,931.
(60) Provisional application No. 60/044,768, filed on Apr. 16, 1997.

(51) Int. Cl.[7] .............................................. C07C 233/07
(52) U.S. Cl. ...................................... 564/123; 564/502
(58) Field of Search ................................. 564/123, 502

(56) References Cited

U.S. PATENT DOCUMENTS

| | | | |
|---|---|---|---|
| 3,056,784 A | 10/1962 | Carr et al. | ................... 260/250 |
| 3,135,794 A | 6/1964 | Archer et al. | ................ 260/562 |
| 4,118,298 A | 10/1978 | Via | ........................ 204/159.18 |
| 5,514,694 A | 5/1996 | Powers et al. | ............... 546/335 |

FOREIGN PATENT DOCUMENTS

| | | |
|---|---|---|
| DE | 1912581 | 9/1969 |
| EP | 0453658 | 10/1991 |
| EP | 0512352 | 11/1992 |
| WO | WO 97/09308 | 3/1997 |
| WO | WO 98/21186 | 5/1998 |
| WO | WO 98/25883 | 6/1998 |

OTHER PUBLICATIONS

Bergman et al., "Studies of the Reaction Between Indole–2, 3–diones (Isatins) and Secondary Aliphatic Amines", *ACTA Chemica Scandinavica*, 51:753–759 (1977).

Bergman et al., "Synthesis of 5H–Pyrazino[2,3–b] indoles from Indole–2,3–dione Derivatives", *ACTA Chemica Scandinavica*, 51:742–752 (1977).

*Primary Examiner*—Richard L. Raymond
*Assistant Examiner*—Venkataraman Balasubramanian
(74) *Attorney, Agent, or Firm*—Fish & Richardson P.C.

(57) ABSTRACT

The invention is based on new methods for making and using compounds and arrays of novel α-ketoamides, and the arrays and compounds made by these methods. These novel compounds are potential inhibitors of proteolytic enzymes, particularly cysteine proteases such as cruzain. Application of the new methods has led to the identification of a number of new inhibitors, from amongst an array of about 38,000 α-ketoamide derivatives, having specific activity against three cysteine proteases: cruzain, papain, and cathepsin B. These compounds and other compounds identified by the methods described herein can be useful, for example, in developing pharmaceutical agents for the treatment of diseases (e.g., Chagas' disease) associated with these proteases. Although the disclosed compounds have specific activity for cruzain, papain, cathepsin B, the methods described herein can also be used to identify inhibitors of other proteases.

11 Claims, 6 Drawing Sheets

| Assay | Cathepsin B | | Cruzain | | Thrombin | | Factor Xa | | 92kDa Gelatinase | |
|---|---|---|---|---|---|---|---|---|---|---|
| Chemistry | >75% | Hit Rate | >75% | Hit Rate | >75% | Hit Rate | >50% | Hit Rate | >75% | Hit Rate |
| α-ketoamide + AMOs | 3 | 0.0500% | 525 | 8.8000% | 0 | 0.0000% | 0 | 0.0000% | 0 | 0.0000% |
| α-ketoamide + triazines | 43 | 0.4500% | 2835 | 30.0000% | 0 | 0.0000% | 0 | 0.0000% | 0 | 0.0000% |
| α-ketoamide + thioureas | 2 | 0.0600% | 307 | 9.5900% | N.D. | | N.D. | | 0 | 0.0000% |
| 38,000 α-ketoamides | 55 | 0.7640% | 3859 | 8.3328% | 0 | 0.0000% | 0 | 0.0000% | 0 | 0.0000% |
| 130,000 non-α-ketoamides | 27 | 0.0273% | 2573 | 2.6015% | 0 | 0.0000% | 2 | 0.0069% | 3 | 0.0036% |

FIG. 3

| ID | Structure | Cruzain IC$_{50}$ | Cathepsin B IC$_{50}$ |
|---|---|---|---|
| 1 | 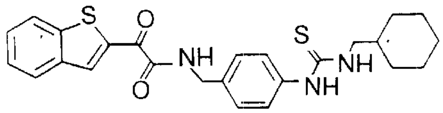 | 0.7 µM | 2.8 µM |
| 2 | 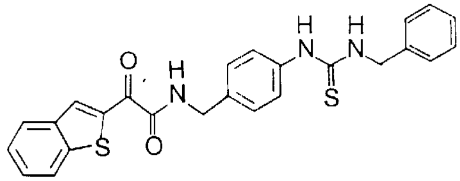 | 2.2 µM | 3.3 µM |
| 3 | 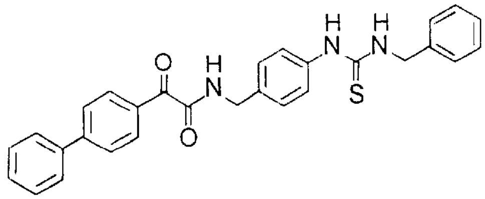 | 0.8 µM | 2.6 µM |
| 4 | 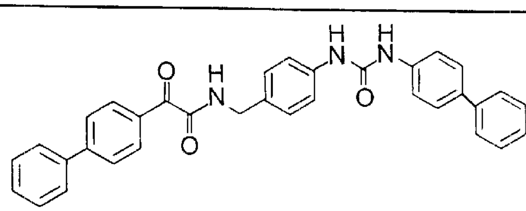 | 0.07 µM | 0.7 µM |
| 5 | 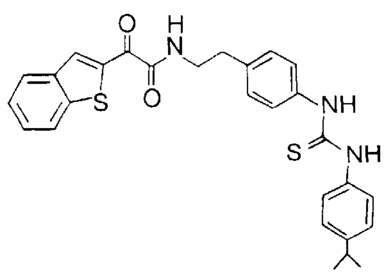 | 0.08 µM | 1.8 µM |
| 6 | 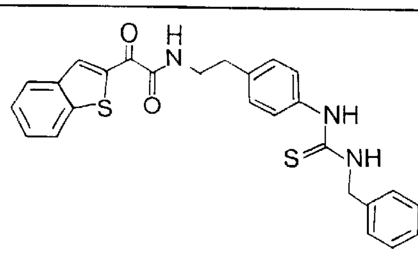 | 1.5 µM | 4.4 µM |

FIG. 4

| Compound | Inhibition (%) at 1 µM ArQule Compound Concentration (n=4) | | | | | | |
|---|---|---|---|---|---|---|---|
| | Cruzain | Thrombin | 92 K | Plasmin | Trypsin | TACE |
| 1 | 86 | -1 | -6 | 0 | -1 | 15 |
| 2 | 16 | -2 | -5 | 0 | -1 | 26 |
| 3 | 53 | -1 | -1 | -2 | 1 | -7 |
| 4 | 100 | 2 | 3 | -7 | -1 | 25 |
| 5 | 97 | 2 | -3 | 0 | -1 | 4 |
| 6 | 51 | -1 | -1 | -5 | 0 | 4 |

FIG. 5

SYNTHESIS AND USE OF α-KETOAMIDE DERIVATIVES AND ARRAYS

CROSS REFERENCE TO RELATED APPLICATIONS

This application is a continuation of U.S. application Ser. No. 09/061,752, filed Apr. 16, 1998, now U.S. Pat. No. 6,143,931, which is a continuation-in-part of provisional application Ser. No. 60/044,768, filed Apr. 16, 1997.

FIELD OF THE INVENTION

The invention relates to non-peptidic α-ketoamide compounds and molecular arrays of potential protease inhibitors and the uses thereof.

BACKGROUND OF THE INVENTION

Proteolytic enzymes, or proteases, are proteins that catalyze the degradation of peptide bonds in protein and peptide substrates. Proteases are typically categorized into four major classes (i.e., serine, aspartyl, metallo, and cysteine), classified according to the catalytic site chemical group that facilitates peptide bond hydrolysis. Proteases are involved in a wide variety of physiological and pathological processes including blood coagulation, protein turnover, complement activation, hormone processing, and cancer cell invasion.

Cysteine proteases, for example, are utilized by living organisms to perform a variety of key cellular functions, and thus are potential targets for drug discovery. For example, cathepsin B has been studied for its role in the progression of normal tissue to cancerous tissue, and the protease cruzain is believed to be essential for the parasitic infection in Chagas' disease (a major public health problem in South and Central America, affecting about 25% of the population of those regions).

The interaction of a protease with a substrate is a highly specific binding event that is driven by, for example, favorable molecular shape recognition (i.e., between the protease and the substrate) and electrostatic e.g., charge-charge, dipolar, or van der Waals) interactions that occur upon binding. Recognition and binding typically involves 3 to 4 amino acid residues of the substrate on either side of an enzyme's catalytic site. Although the kinetics of all proteolytic events are not fully understood, most protease-mediated catalysis occurs because the catalytic site stabilizes a transition-state, structural intermediate in the pathway to peptide-bond cleavage.

Inhibitors of proteolytic activity typically interact with a protease at its active site, preventing interaction (e.g., recognition, binding, or reaction) of enzyme and substrate. However, inhibition via allosteric change (i.e., conformational or other structural change) and co-factor binding inhibition are some other possible modes of inhibition. Potent and specific synthetic inhibitors can: 1) interact with the enzyme's binding pocket with high affinity, and 2) interact with the catalytic site to mimic the transition state structure.

Modulation, e.g., inhibition or enhancement, of protease activity can profoundly influence biological systems, and, therefore, proteases are often chosen as targets for drug discovery. In the design of protease inhibitors, researchers have generally identified chemical structures that interact with the catalytic chemical group at the active site of the protease and find structures that mimic the transition state of the catalytic reaction. These identified structures are then linked to a di- or tri-peptide sequence that specifically binds to the active site substrate binding pockets. Peptide-based inhibitors, mimicking the primary sequence of the natural substrate, often show very high potency against the target; however, orally administered peptides generally exhibit poor bioavailability due to hydrolysis by nonspecific proteolytic enzymes in the digestive system. Substitution of the peptide portion of protease inhibitors with small organic molecules that mimic the molecular shape and charge interactions of the peptides frequently results in improved bioavailability and oral absorption for that inhibitor.

SUMMARY OF THE INVENTION

The invention is based on new methods for making and using compounds and arrays of novel α-ketoamides, and the arrays and compounds made by these methods. These novel compounds are potential inhibitors of proteolytic enzymes, particularly cysteine proteases such as cruzain. Application of the new methods has led-to the identification of a number of new inhibitors, from amongst an array of about 38,000 α-ketoamide derivatives, having specific activity against two cysteine proteases: cruzain and cathepsin B. These compounds and other compounds identified by the methods described herein can be useful, for example, in developing pharmaceutical agents for the treatment of diseases (e.g., Chagas' disease) associated with these proteases. Although the disclosed compounds have specific activity for cruzain and cathepsin B, the methods described herein can also be used to identify inhibitors of other proteases.

In one embodiment, the invention features a method for preparing a monoacylated diamine compound. The method includes the step of reacting a diamine with an α-ketoester compound, under conditions such that a monoacylated diamine is prepared. The diamine can be represented, for example, by the structure B—NH—Y—NH—C, where Y is a linker moiety (i.e., a divalent alkyl, carbocyclic, or aryl groups), and B and C can independently be hydrogen, an alkyl group, a carbocyclic group, or an aryl group. The α-ketoester can be represented, for example, by the structure:

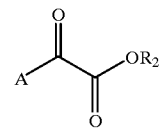

where A and $R_2$ can independently be an alkyl group, a carbocyclic group, or an aryl groups.

A functionalized α-ketoamide compound can also be formed, for instance, by preparing a monoacylated diamine by the above method, then reacting the monoacylated diamine with an electrophile (e.g., an alkoxymethylene oxazolone, an acid halide, an isocyanate, an isothiocyanate, an anhydride, a halotriazine, a Michael acceptor, an aldehyde, or a ketone).

In another embodiment, the invention features a method for preparing a plurality (e.g., 100 or more, or 1000 or more) of α-ketoamide compounds. The method includes the step of reacting a plurality of diamine compounds with a plurality of α-ketoester compounds, under conditions whereby a plurality of α-ketoamide compounds is prepared.

The plurality of diamines can include, for example, a diamine that can be represented by the structure B—NH—Y—NH—C, where Y, B, and C are defined as above. Each of the α-ketoester compounds can be, for example, represented by the structure:

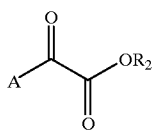

wherein A and $R_2$ are defined as above.

The method can also include the step of reacting the plurality of α-ketoamide compounds with a plurality of electrophiles (alkoxymethylene oxazolones, acid halides, isocyanates, isothiocyanates, anhydrides, halotriazines, Michael acceptors, aldehydes, ketones, or combinations thereof), such that a plurality of functionalized α-ketoamide compounds is prepared.

The plurality of compounds can, for example, be arranged in a spatially addressable array format. An array produced by this method is contemplated.

Still another embodiment of the invention features an array of α-ketoamide compounds. Each of the α-ketoamide compounds can be represented, for example, by the formula:

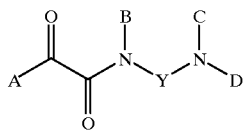

where A can be an alkyl group, a carbocyclic group, or an aryl group; B and C independently can be hydrogen, an alkyl group, a carbocyclic group, or an aryl group; Y can be a divalent alkyl group, carbocyclic group, or aryl group; and D can be hydrogen, an alkyl group, a carbocyclic group, an aryl group, or —C(X)—Z—W, where X is O or S, Z is a single bond or NR; and R and W independently can be hydrogen, an alkyl group, a carbocyclic group, or an aryl group.

The array can include, for example, at least about 100 compounds, or at least about 1000 compounds.

D can be, for example, the triazolinyl moiety:

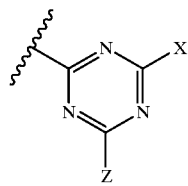

where X and Z independently can be an unsubstituted, monosubstituted, or disubstituted amino group, a thioalkyl group, a thioaryl group, an alkoxy group, an aryloxy group, a halogen (e.g., F, Cl, Br, or I), an alkyl group, a carbocyclic group, or an aryl group.

Alternatively, D can be the oxazolinyl moiety:

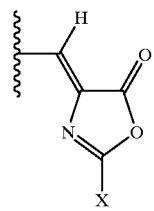

where X can be an alkyl group, a carbocyclic group, or an aryl group.

A method of identifying a compound having a specific characteristic (e.g., inhibition of an enzyme, or other biological activity or interaction) is also contemplated. The method includes screening any of the arrays described above with an assay capable of detecting the presence of a compound having the specific characteristic. For example, compounds that inhibit proteases (e.g., a serine protease such as α-thrombin, Factor Xa, plasmin, or trypsin; a cysteine protease such as cruzain, cathepsin B, cathepsin K, papain, or calpain; a metalloprotease such as TACE or 92 kDa gelatinase; or an aspartyl protease) can be identified.

Yet another embodiment of the invention features a non-peptidyl compound represented by the formula:

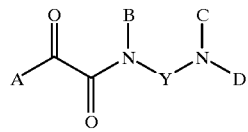

where A–D and Y are as defined above. In particular, the compound can have, for example, one of the following six structures:

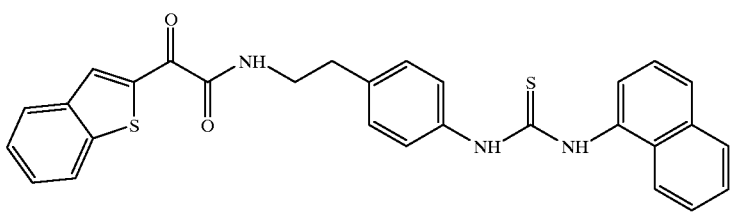

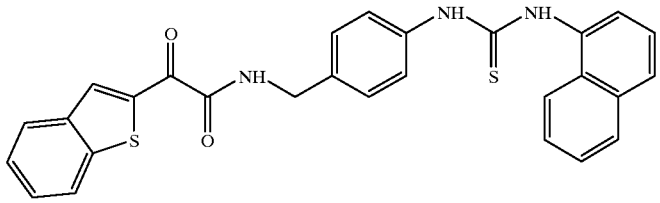

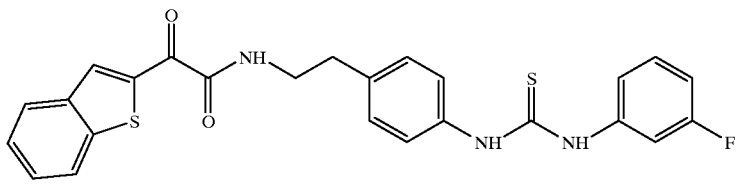

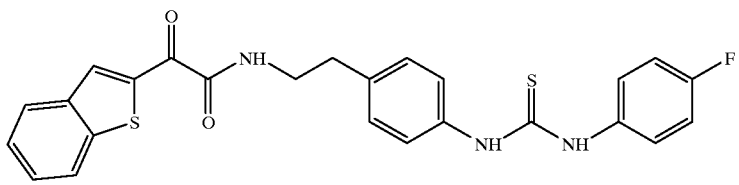

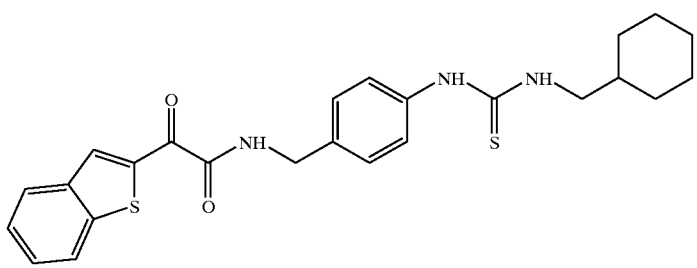

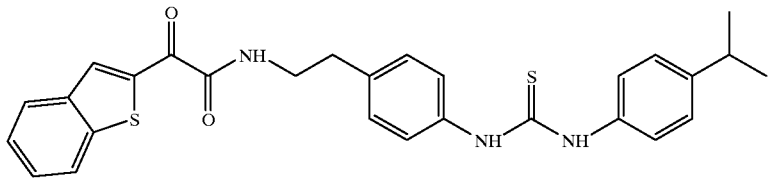

The compound can be, for example, an inhibitor of a cysteine protease such as cruzain.

Alternatively, D can represent the triazolinyl moiety:

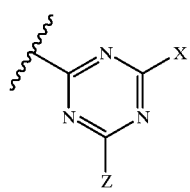

wherein X and Z are as defined above for triazolinyl moieties; or the oxazolinyl moiety:

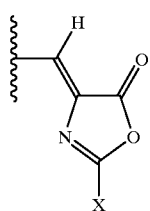

wherein X is defined as above for oxazolinyl moieties.

In some cases, A can be either 2,4-difluorophenyl or 4-nitrophenyl. Y can be a $C_2$–$C_6$ alkylene. D can be hydrogen, and B and C can be identical.

For example, A can be 3-trifluoromethylphenyl, phenyl, 4-bromophenyl, 2,4-difluorophenyl, 4-nitrophenyl, 4-tert-butylphenyl, 3-tolyl, 3-methoxyphenyl, 3-fluorophenyl, or 4-methoxyphenyl; D can be 2-thienyl, 2-naphthyl, p-biphenyl, m-tolyl, 4-trifluoromethylphenyl, 2-furyl, 2-chlorophenyl, o-tolyl, 4-t-butylphenyl, 3-methoxyphenyl, 2,4-dichlorophenyl, 3-nitrophenyl, 4-bromophenyl, 1-naphthyl, 3-furyl, 3,4-methylenedioxyphenyl, 3-pyridyl, p-tolyl, 4-chlorophenyl, or 4-nitrophenyl; and the combination of Y, B, and C can be selected from one of the following combinations: Y is ethyl and B and C are methyl; Y is propyl and B and C are methyl; Y is hexyl and B and C are methyl; Y, B, C, and the two nitrogen atoms form a piperazine; Y, B, C, and the two nitrogens form a homopiperazine; Y is butyl and B and C are hydrogen; Y is cyclohexyl attached to the nitrogens at the 1 and 3 positions and B and C are methyl; or Y is propyl and B and C are hydrogen. Y can be ethylbenzene-2',4-diyl or toluene 1',4-diyl.

In some cases, Y can be ethylbenzene-2',4-diyl or toluene 1',4-diyl. A can be 2-benzo[b] thienyl. B and C can both be hydrogen.

A composition comprising any of the above compounds together with an acceptable (i.e., pharmacologically safe) excipient in also contemplated, as is a method of treating a subject suffering from Chagas' disease by administering to the subject an effective protease-inhibiting amount of any of the above compositions.

Another embodiment of the invention features a method for inhibiting a protease (e.g., a serine protease, or a cysteine protease such as cruzain). The method includes the steps of contacting the protease with a compound represented by the formula:

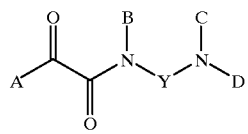
where A–D and Y are defined as above.
In a specific example, the compound can have one of the following six structures:
In another embodiment, the invention features a method for making an α-ketoamide aminomethylene oxazolone. The method includes the steps of reacting a diamine of formula:
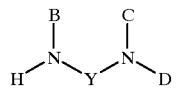
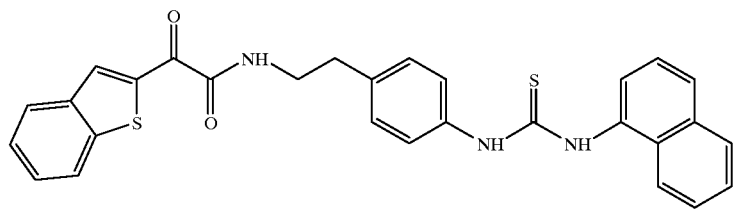
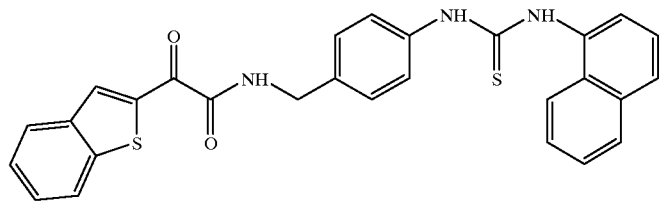
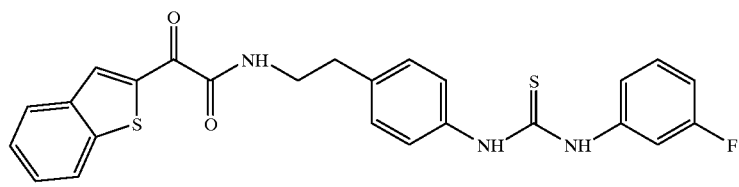
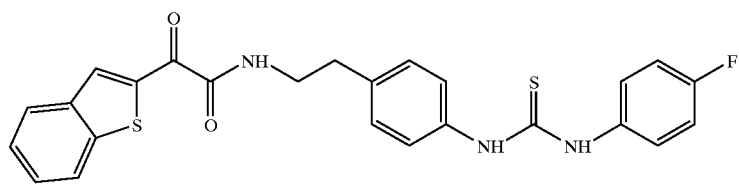
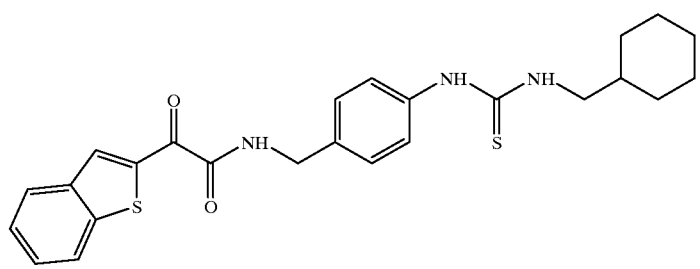
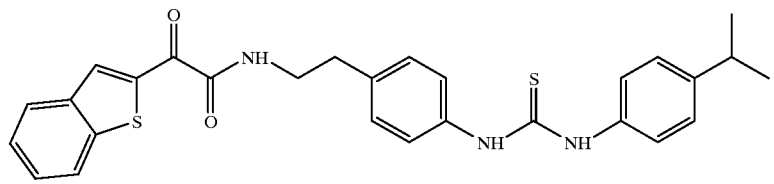

with an α-ketoester of formula:

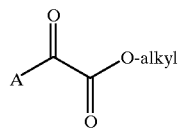

to form an α-ketoamide; and then reacting the α-ketoamide with an alkoxymethylene oxazolone of formula:

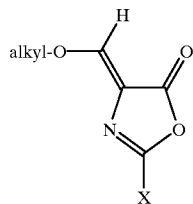

where A–D and Y are as defined above.

For example, the diamine can be ortho-aminobenzoylamine, meta-aminobenzoylamine, para-aminobenzoylamine, N,N'-dimethyl-1,2-ethylenediamine, N,N'-dimethyl-1,3-propanediamine, N,N'-dimethyl-1,6-hexanediamine, piperazine, homopiperazine, 1,4-diaminobutane, 1,3-cyclohexanebis(methylamine), or 1,3-diaminopropane; the α-ketoester can be alkyl 3-trifluoromethylbenzoylformate, alkyl benzoylformate, alkyl 4-bromobenzoylformate, alkyl 2,4-difluorobenzoylformate, alkyl 4-nitrobenzoylformate, alkyl 4-tert-butylbenzoylformate, alkyl 3-methylbenzoylformate, alkyl 3-methoxybenzoylformate, alkyl 3-fluorobenzoylformate, or alkyl 4-methoxybenzoylformate (where alkyl is methyl, ethyl, or other unhindered or activated aliphatic substituent to form an α-ketoamide); and the alkoxymethylene oxazolone can be 2-thienyl alkoxymethylene oxazolone, 2-naphthyl alkoxymethylene oxazolone, p-biphenyl alkoxymethylene oxazolone, m-tolyl alkoxymethylene oxazolone, 4-trifluoromethylphenyl alkoxymethylene oxazolone, 2-furyl alkoxymethylene oxazolone, 2-chlorophenyl alkoxymethylene oxazolone, o-tolyl alkoxymethylene oxazolone, 4-t-butylphenyl alkoxymethylene oxazolone, 3-methoxyphenyl alkoxymethylene oxazolone, 2,4-dichlorophenyl alkoxymethylene oxazolone, 3-nitrophenyl alkoxymethylene oxazolone, 4-bromophenyl alkoxymethylene oxazolone, 1-naphthyl alkoxymethylene oxazolone, 3-furyl alkoxymethylene oxazolone, 3,4-methylenedioxyphenyl alkoxymethylene oxazolone, 3-pyridyl alkoxymethylene oxazolone, p-tolyl alkoxymethylene oxazolone, 4-chlorophenyl alkoxymethylene oxazolone, or 4-nitrophenyl.

Yet another embodiment of the invention is a method for making an α-ketoamide thiourea. The method includes the steps of reacting a diamine of formula:

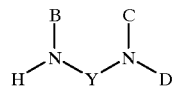

with an α-ketoester of formula:

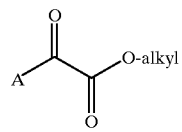

to form an α-ketoamide; and reacting the α-ketoamide with an isothiocyanate of formula:

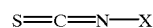

where A–D and Y are defined as above.

An array of compounds is also contemplated, where each of the compounds in the array is prepared according to one of the above methods.

"Structural diversity elements" are chemical functional groups and can include linear chain or branched chain alkyl groups, carbocyclic groups, aryl groups, and heteroatomic functional groups such as nitro groups, sulfonyl groups, and other nitrogen, oxygen, sulfur, or halogen bearing groups. In an array that includes a plurality of compounds, structural diversity elements are the variable parts of the compound. In contrast, the "molecular core structure" is invariant, common to each compound in the array.

The terms "bonded," "binding," "binds," or "bound," as used herein, can refer to, for example, covalent, ionic, van der Waals, or hydrophobic interactions. Coordination complexes and hydrogen bonding are also contemplated. Typically, the bonding interactions are reversible, but can be irreversible in some cases.

"Alkyl groups" should be construed to include both linear chain and branched chain derivatives of any substituted or unsubstituted acyclic carbon-containing moieties, including alkanes, alkenes, and alkynes. Alkyl groups having one to five, ten, twenty, or even more carbon atoms are possible. Examples of alkyl groups include lower alkyls, for example, methyl, ethyl, n-propyl, iso-propyl, n-butyl, iso-butyl, tert-butyl; higher alkyls, for example, octyl, nonyl, and decyl; lower alkenyls, for example, ethenyl, propenyl, propadienyl, butenyl, butadienyl; higher alkenyls such as 1-decenyl, 1-nonenyl, 2,6-dimethyl-5-octenyl, and 6-ethyl-5-octenyl; and alkynyls such as 1-ethynyl, 2-butynyl, and 1-pentynyl. Other linear and branched alkyl groups are also within the scope of the present invention.

In addition, such alkyl groups can also contain various substituents in which one or more hydrogen atoms has been replaced by a functional group. Functional groups include, but are not limited to, tertiary amine, amide, ester, ether, and halogen, i.e., fluorine, chlorine, bromine and iodine. Specific substituted alkyl groups can be, for example, alkoxy such as methoxy, ethoxy, butoxy, and pentoxy; dimethylamino, diethylamino, cyclopentylmethylamino, benzylmethylamino, and dibenzylamino; formamido, acetamido, or butyramido; methoxycarbonyl or ethoxycarbonyl; or dimethyl or diethyl ether groups.

"Carbocyclic groups" include both substituted and unsubstituted, cyclic, carbon-containing moieties such as cyclopentyl, cyclohexyl, cycloheptyl, and adamantyl. Such cyclic groups can also contain various substituents in which one or more hydrogen atoms have been replaced by a functional group. Such functional groups include those described above, as well as lower alkyl groups as described above. The cyclic groups of the invention can also include one or more heteroatoms, for example, to form heterocyclyls.

"Aryl groups" include substituted and unsubstituted hydrocarbon rings bearing a system of conjugated double bonds, usually comprising (4n+2) pi bond electrons, where n is an integer equal to or greater than 0. Examples of aryl groups include, but are not limited to, phenyl, naphthyl, anisyl, tolyl, xylyl and the like. Aryl groups can also include aryloxy, aralkyl, aralkyloxy and heteroaryl groups, e.g., pyrimidine, morpholine, piperazine, piperidine, benzoic acid, toluene, thiophene, and the like. These aryl groups can also be substituted with any number of a variety of functional groups. In addition to the functional groups described above in connection with substituted alkyl groups and carbocyclic groups, functional groups on the aryl groups can also include other nitrogen, oxygen, sulfur, or halogen bearing groups.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and are not intended to be limiting.

An advantage of the new α-ketoamide-based inhibitors is that they are non-peptidyl. Low molecular weight organic molecules are often superior to peptidyl compounds as protease inhibitors, primarily due to such factors as their stability in the acidic environment of the digestive system, good transport into the vascular system, and high bioavailability to the target tissue. The new compounds and arrays disclosed herein can lead to the identification of new classes of potentially reversible protease inhibitors that are both potent and specific. For example, potent in vitro inhibitors of the cysteine protease cruzain are disclosed herein.

In addition, the α-ketoamide-based inhibitors appear to demonstrate reversible binding kinetics. The pharmacokinetics (i.e., tissue-residence time, renal clearance) of reversible inhibitors are generally superior to those of irreversible inhibitors in target tissue. For example, these properties allow a physician to more easily maintain therapeutic doses of the drugs in the patient's serum. Thus, the new α-ketoamide-based inhibitors are potentially superior to the known cysteine protease inhibitors (e.g., chloromethylketones, epoxy-succinyl compounds, and vinyl sulfones), all of which bind irreversibly.

Other features and advantages of the invention will be apparent from the following detailed description, and from the claims.

BRIEF DESCRIPTION OF THE DRAWINGS

FIG. 3 is a table that lists primary screening results for arrays screened against five proteases.

FIG. 4 is an illustration of six compounds (1–6) and their respective $IC_{50}$ values for inhibition of cruzain and cathepsin B.

FIG. 5 is a table that lists percentage inhibition of cruzain and five other proteases by compounds 1–6.

DETAILED DESCRIPTION

The invention provides new methods for making arrays of novel α-ketoamide compounds. These methods can be used, for example, to generate arrays of potential inhibitors of proteolytic enzymes. The new arrays include the α-ketoamide molecular core structure shown in FIG. 1A or a derivative thereof, as shown in FIGS. 1B–1D. By screening an array of about 38,000 α-ketoamide compounds produced by the new methods against all four major classes of proteases (i.e., serine, metallo-, aspartyl, and cysteine), a subset of these compounds was identified as having a strong affinity toward cysteine proteases, especially cruzain.

Methods of Making Arrays and Individual Compounds

Compounds of the invention can be prepared by reacting components to form the α-ketoamide-derived molecular core structure and structural diversity elements. Thus, during synthesis, "components" are used to make the "members" or "individual compounds" of an array, and the terms "molecular core" (or "molecular core structure") and "diversity element" (or "structural diversity element") are used herein to describe the parts of the completed compounds of an array.

The members of the new arrays can be constructed from a wide variety of reaction components. Each component can form a part or all of a molecular core structure or structural diversity element. Thus, components can be added to reactive sites on a preexisting molecular core structure to form or attach structural diversity elements.

On the other hand, the molecular core structure and the structural diversity elements can, in some cases, be formed from a combination of two or more components. For example, one component can include a portion of a molecular core structure and also a partial or complete structural diversity element, while a second component can include the remainder of the molecular core structure together with any remaining structural diversity elements.

Figure 1A:
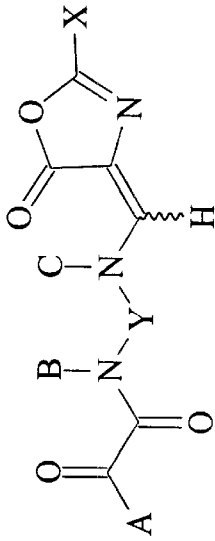
FIGS. 1A–1D are, respectively, drawings of a generic α-ketoamide molecular core structure, and aminomethylene oxazolone (AMO), triazine, and thiourea derivatives thereof.
Figure 1B:
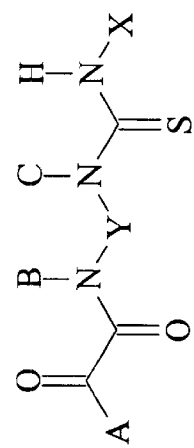
Figure 1C:
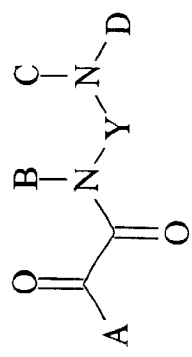
Figure 1D:
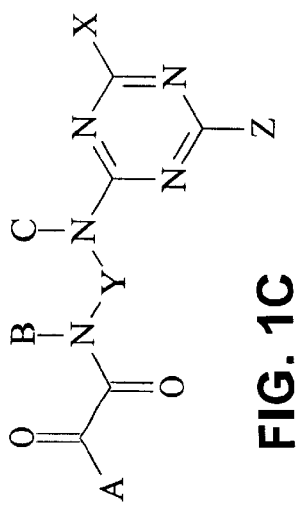

The compounds described herein have a molecular core structure based on the α-ketoamide formula shown in FIG. 1A. This core structure provides attachment points for at least four structural diversity elements, i.e., A, B, C, and D, and allows for variation of linker Y.

The compounds can be constructed from the monoacylation of diamines by α-ketoesters, using the following synthetic method:

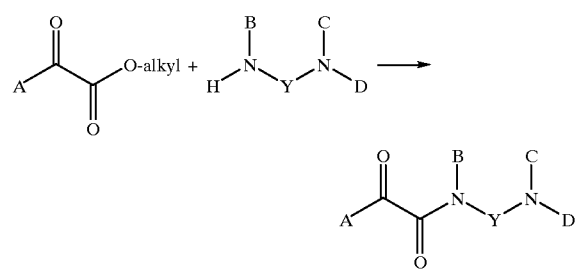

where A, B, C, and Y are structural diversity elements as described above. Structural diversity element D can be the same as or different from A, B, and C, and can be hydrogen, a straight or branched chain alkyl group, a carbocyclic group, an aryl group, or a substituted or heterocyclic derivative thereof.

When both C and D are not hydrogen, the compound contains a tertiary amine, and, thus, is only capable of a single acylation reaction. Therefore, the α-ketoamide formed by reaction of an α-ketoester and a diamine containing a tertiary amine is not capable of undergoing further acylation of the terminal amine. When structural diversity element D is hydrogen, the terminal amine is a primary or secondary amine, either of which permits further reaction of the α-ketoamide with an electrophile.

The diamine can have, for example, a carbon chain of from about 2 to about 6 or more carbon atoms connecting the nitrogen atoms; the α-ketoester can be, for example, a methyl, ethyl, or other activated (e.g., trifluoromethyl) or unhindered aliphatic ester, or thioesters.

It was discovered during the preparation of simple α-ketoamides from the corresponding methyl α-ketoesters that good yields of monofunctionalized products were obtained with equimolar amounts of a primary amine and the methyl α-ketoesters. However, for secondary amines, complete conversion requires excess amine, typically two equivalents. Without being bound by theory, it is believed that this observation can be attributed to hemiaminal formation. Even though hemiaminal formation is reversible, it can tie up a considerable amount of the amine. This implies that symmetrical diamines can experience in situ protection, resulting in mono-acylation.

Experimentally, it was found that high yield mono-acylation occurs with both secondary and primary amines. Mono-acylation is advantageous for several reasons. For example, mono-acylation enables the preparation of relatively pure products from the reaction of an α-ketoester with a single equivalent of a symmetrical diamine, without the need for amino protecting groups. The procedure also results in high regioselectivity with the use of non-symmetrical diamines. Moreover, mono-acylation leaves the unreacted end of the diamine free for further modification. Thus, once the mono-acylated compound has been formed, other reactions involving the unreacted amino group of the diamine can be carried out. For example, the unreacted amino group can react with electrophiles such as alkoxymethylene oxazolones, acid chlorides, sulfonyl chlorides, carboxylic acid anhydrides, isocyanates, or isothiocyanates. The unreacted amino groups can also participate in the Mannich reaction, oxazolone ring opening reactions, the cyclic sulfate reaction, or triazine reactions. Reaction of the non-acylated amino group can be used either for introducing structural diversity elements to the basic α-ketoamide molecular core structure, or to make more elaborate molecular core structures such as the α-ketoamide aminomethylene oxazolone molecular core structure of FIG. 1B, the α-ketoamide triazine molecular core structure of FIG. 1C, or the α-ketoamide thiourea molecular core structure of FIG. 1D.

In a general synthesis of α-ketoamide-thiourea compounds (FIG. 1D), for example, α-ketoesters (1.0 equivalent) were combined with diamines (1.0 equivalent) in a solvent at a concentration of 0.5 M. The reaction mixtures were shaken vigorously and then allowed to stand at 25° C. for 24–96 hours. The solvent was removed under reduced pressure and the resulting mono-α-ketoamide intermediates were dissolved in a solvent (0.25–0.3 M), for example, an aprotic solvent such as DMSO, THF, or DMF. The mono-α-ketoamide intermediates were then treated with isothiocyanates (1.0 equivalent) neat or dissolved in the same solvent (0.25 M) to provide a final concentration of 0.125–0.3 M. The reaction mixtures were then sealed and heated at 85° C. for 24–48 hours.

The methods described above can also be used to synthesize α-ketoamide compounds in the construction of an array. Laboratory-scale robotic devices can be used to automate the unit operations of the organic chemical syntheses. The analysis of the synthesis products can be integrated into automated synthesis as an on-line quality control function, with automated data acquisition and storage, and historical process analysis.

A 96-well microtiter-type spatial format plate can serve as the foundation for the management of both high throughput screening data and chemical synthesis data. Organic compounds arrayed in alphanumerically registered 96-well plates are specified by descriptors derived from row, column, and plate numbers. The descriptors are ideally suited for electronic storage and retrieval from chemical and biological databases. This format allows high throughput bioassays for inhibition of a biological target to be performed with the chemical arrays and provides insights into structure activity relationships of the chemical arrays.

Testing the Compounds

The α-ketoamide compounds of the invention can be tested for a property of interest (e.g., biological activity), using methods known to those of ordinary skill in the art. For example, the compounds can be tested for inhibition of proteolytic enzymes as described in the Examples provided below. In a preferred embodiment, the compounds are screened in a format in which the compounds are logical ordered in a spatially arranged array according to the methods described in U.S. Pat. No. 5,712,171. These methods can generate a pattern of activity data (see, e.g., FIG. 6), providing structure-activity relationship information that can facilitate optimization of active compounds.

Therapeutic Applications

The new methods and arrays can be used to identify lead compounds useful for treating humans or animals afflicted with Chagas' disease or other diseases that are subject to therapeutic intervention by inhibition of a protease. For example, the HIV I protease has been identified as a target of therapeutic intervention in AIDS, and many HIV I protease inhibitors have been developed and demonstrated co have a therapeutic effect. Another example is the protease cathepsin K, inhibition of which is believed to have a therapeutic effect on osteoporosis.

A therapeutically effective amount of the compound is the quantity of compound that, after being administered to an individual with Chagas' disease, for example, brings about an amelioration of the disease processes and conditions associated with long-term infection by *T. cruzi* (i.e., the etiological agent of Chagas' disease) without causing unacceptable side effects. Ameliorating the disease processes and conditions associated with Chagas' disease can include decreasing parasitic load in the infected individuals' target organs (e.g., in the digestive system, cardiovascular system, or nervous system) or decreasing cellular disruption due to parasite replication in the tissues. Amelioration can also include slowing of the myocarditis often present due to the destruction of cardiac tissue and associated ganglia, or reducing the megasyndromes of Chagas' disease due to distention or enlargement of the esophagus or intestine.

The practitioner can determine the appropriate dosage for administration to a human or veterinary patient. The amount of a compound that is administered will depend on a number of factors, including the general health, size, age, and gender of the individual, as well as the route of administration. It will also depend on the degree, location, and severity of the individual's infection by the parasite. Typically, however, between about 100 μg and 5 g of the compound can be administered to the individual per day. For example, about 1 to 1000 mg (e.g., 1 to 100 mg or 1 to 30 mg) can be administered orally (e.g., in the form of a pill, tablet, syrup, suspension, or capsule) each day. The compound can also be administered intravenously (e.g., by injection) into the systemic vascular compartment. Still other appropriate modes of administration include systemic administration, intramuscular, intradermal, subcutaneous, and intraperitoneal administration. The compound can also be applied topically at the site of suspected infection by the insect that acts as the vector for the parasite.

Compounds identified by the new methods described herein can be administered to the individual in connection with an acceptable pharmaceutical carrier as part of a pharmaceutical composition for treating infection.

Suitable pharmaceutical carriers can contain inert ingredients that do not interact with the compound. Standard pharmaceutical formulation techniques may be employed such as those described in Remington's Pharmaceutical Sciences (Mack Publishing Company, Easton, Pa.). Suitable pharmaceutical carriers for intravenous and other parenteral administration include, for example, sterile water, physiological saline, bacteriostatic saline (i.e., saline containing about 0.9% mg/ml benzyl alcohol), phosphate-buffered saline, Hank's solution, or Ringer's lactate. Methods for encapsulating compositions (such as in a coating of hard gelatin or cyclodextran) are known in the art (Baker, et al., "Controlled Release of Biological Active Agents", John Wiley and Sons, 1986). Suitable carriers for topical administration include commercially available inert gels, liquids supplemented with albumin, methyl cellulose, or a collagen matrix. Typical of such formulation are ointments, creams, and gels. Preferred carriers for topical administration are those which facilitate penetration of the skin by the new compound.

Compounds identified by the new methods can also be administered as at least one physiologically acceptable salt such as a chloride salt, a bromide salt, or an acetate salt.

In addition to the compounds of interest, another pharmacologically active agent can be included in the preparation. Chagas' disease is currently treated by two compounds, Nifurtimox and Benznidole, both of which display several negative side-effects. However, it may be advantageous to administer the α-ketoamide derivatives with these existing treatments or other anti-protozoal agents.

The invention is further described in the following examples, which do not limit the scope of the invention described in the claims.

EXAMPLES

Example 1

In the synthesis of a specific α-ketoamide-thiourea compound, methyl-2-(2-benzothienyl)-2-oxoethanoate (500 mg, 2.27 mmol) was combined with 4-aminobenzylamine (2.27 mmol) in methanol (1.0 M). The reaction mixture was shaken vigorously and then allowed to stand at 25° C. for 24 hours. The methanol was removed under reduced pressure to provide the resulting mono-α-ketoamide intermediate in quantitative yield. 50 mg (1.6 mmol) of the intermediate was dissolved in DMSO (0.3 M) and then treated with neat benzyl isothiocyanate (1.6 mmol). The reaction mixture was then sealed and heated at 85° C. for 24 hours. The product was crystallized from ethyl acetate/ether (10/1) to provide a yellow solid (49 mg, 68% yield). The structure and purity were determined by HPLC, MS, and LCMS analyses.

Example 2

Figure 2:
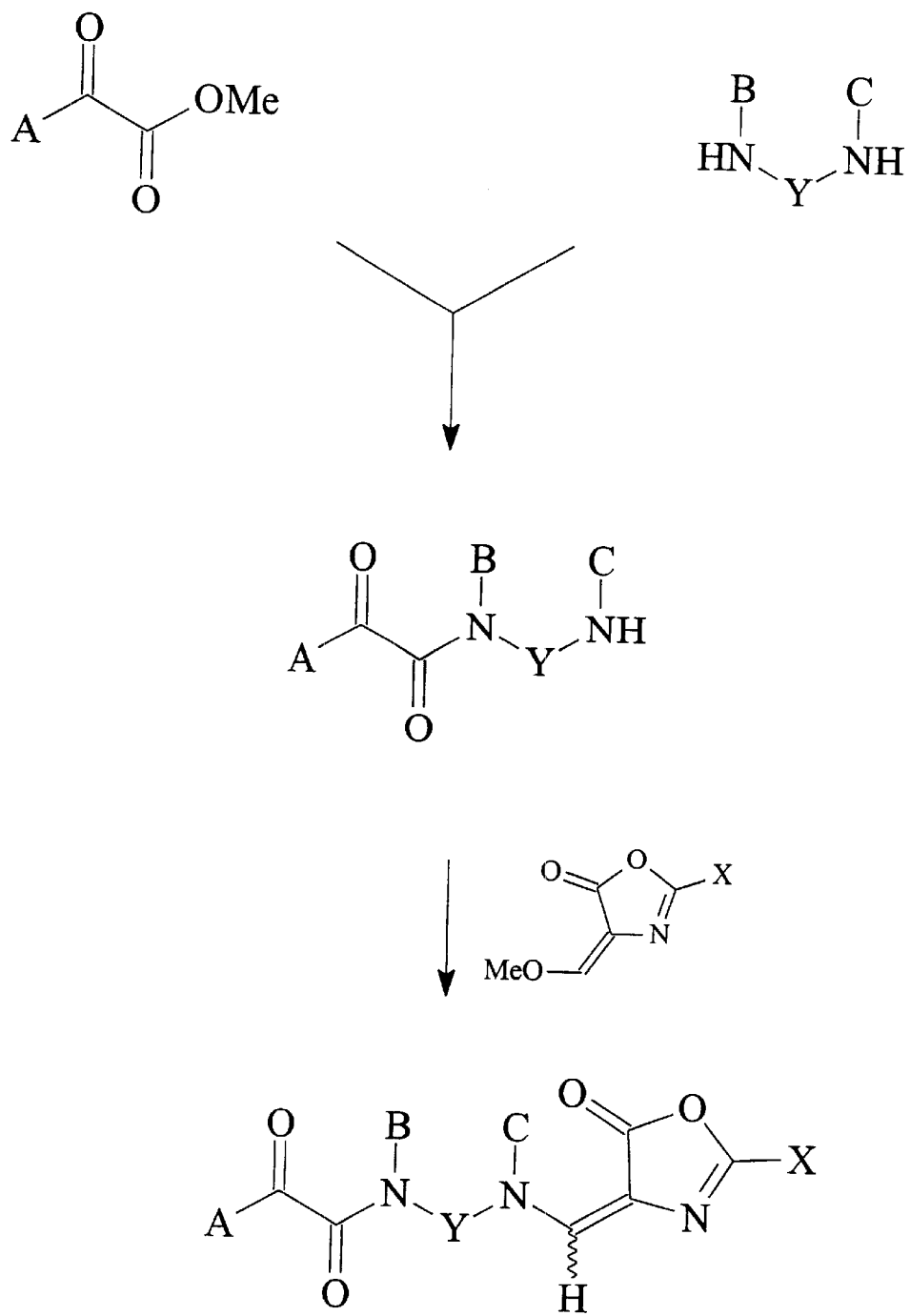
FIG. 2 is a synthetic scheme for making α-ketoamide molecules and AMO derivatives thereof.

An array of 1,600 α-ketoamide-AMO compounds (FIG. 1B) was synthesized using the convergent parallel synthesis scheme shown in FIG. 2, which allowed the entire array to be synthesized from just 38 components (i.e., 10 α-ketoesters, 8 diamines, and 20 ethoxymethylene oxazolones). During the synthesis, the methyl α-ketoesters were discovered to provide clean, high-yield monofunctionalization of the amines. Combinations of stock solutions at standard concentration were prepared at 50 μM for the automated steps of the synthesis.

The α-ketoesters used in the preparation of the array were:

1. methyl 3-trifluoromethylbenzoylformate,
2. methyl benzoylformate,
3. methyl 4-bromobenzoylformate,
4. methyl 2,4-difluorobenzoylformate,
5. methyl 4-nitrobenzoylformate,
6. methyl 4-tert-butylbenzoylformate,
7. methyl 3-methylbenzoylformate,
8. methyl 3-methoxybenzoylformate,
9. methyl 3-fluorobenzoylformate, and
10. methyl 4-methoxybenzoylformate.

The diamines used were:

1. N,N'-dimethyl-1,2-ethylenediamine,
2. N,N'-dimethyl-1,3-propanediamine,
3. N,N'-dimethyl-1,6-hexanediamine,
4. piperazine,
5. homopiperazine,
6. 1,4-diaminobutane,
7. 1,3-cyclohexanebis(methylamine), and
8. 1,3-diaminopropane.

The alkoxymethylene oxazolones (AMO) used were:

1. 2-thienyl AMO,
2. 2-naphthyl AMO,
3. p-biphenyl AMO,
4. m-tolyl AMO,
5. 4-trifluoromethylphenyl AMO,
6. 2-furyl AMO,
7. 2-chlorophenyl AMO,
8. o-tolyl AMO,
9. 4-t-butylphenyl AMO,
10. 3-methoxyphenyl AMO,
11. 2,4-dichlorophenyl AMO,
12. 3-nitrophenyl AMO,
13. 4-bromophenyl AMO,
14. 1-naphthyl AMO,
15. 3-furyl AMO,
16. 3,4-methylenedioxyphenyl AMO,
17. 3-pyridyl AMO,
18. p-tolyl AMO,
19. 4-chlorophenyl AMO, and
20. 4-nitrophenyl AMO.

To carry out the syntheses, methyl α-ketoesters were reacted with diamines. Stock solutions of the α-ketoesters and the diamines were prepared at 0.25 M concentration in methanol. The α-ketoester solutions were dispensed (200 μl, 0.05 mmol), then the diamine solutions (200 μl, 0.05 mmol) were added. The reactions were incubated at 25° C. for 5 days and were then concentrated. The resulting intermediate products were dissolved in DMSO (200 μl, 0.25 M), and then treated with a solution of the appropriate alkoxymethylene oxazolone compounds (0.25 M in DMSO, 200 μl, 0.05 mmol). The reactions were then heated to 80° C. and agitated for 24 hours.

Example 3

Arrays of α-ketoamide-triazine conjugates (9600 compounds; FIG. 1C) and α-ketoamide-thiourea conjugates (3200 compounds; FIG. 1D) were also synthesized using the convergent parallel synthesis described in Example 2, substituting the alkoxymethylene oxazolone precursors with triazolinyl and isothiocyanate precursors, respectively.

To carry out the syntheses, methyl α-ketoesters were reacted with diamines. Stock solutions of the α-ketoesters and the diamines were prepared as above. The α-ketoester solutions were dispensed, then the diamine solutions added. The reactions were incubated for 5 days and were then concentrated at suitable temperatures for handling the triazolinyl and isothiocyanate components. The resulting intermediate products were dissolved in DMSO (200 μl, 0.25 M), and then treated with a solution of the appropriate triazolinyl or isothiocyanate compounds (0.25 M in DMSO, 200 μl, 0.05 mmol). The reactions were then heated and agitated for 24 hours.

Example 4

High-throughput Cathepsin B Assay:

A fluorometric high throughput cathepsin B assay for detecting inhibitory activity was developed in 96-well microtiter plate format. Benzyloxy-Phe-Arg-AMC (Z-F-R-AMC; Molecular Probes, Inc., Eugene, Oreg.) was the substrate used in the assay ($K_m$=150 μM). Cathepsin B (EC 3.4.22.1, from human liver) was purchased from Sigma Chemical Company (St. Louis, Mo.) in a stock solution containing 25 μg of the protein in 25 μl buffer (i.e., 20 mM sodium acetate, pH 5.0, and 1 mM EDTA).

The bioassay of the compounds was performed on a Sagian/Beckman Integrated robotic system (Beckman, Fullerton, Calif.). Inhibition of enzyme activity was measured via fluorescent detection. Fluorescence readings were taken at an excitation wavelength of 390 nm ($\lambda_{max}$=350 nm) and an emission wavelength of 430 nm ($\lambda_{max}$=430 nm) on a BMG FluoStar (BMG, Durham, N.C.). Chemical compounds solubilized in 10.0% dimethyl sulfoxide, (DMSO) were pre-transferred to 96 or 384 well assay plates to yield the indicated final concentration of compound. The assay was carried out at a substrate concentration of 30 μM in an assay buffer (88 mM $KH_2PO_4$, 12 mM $Na_2HPO_4$, 1.33 mM $Na_2EDTA$, pH 6.0) at room temperature (22° C.). All of the reagents and the enzyme were maintained at 22° C. during the assay.

The reaction was initiated by the addition of the cathepsin B (0.46 ng/ml) in the assay buffer containing dithiothreitol (giving a final concentration of 1.5 mM). The final concentration of DMSO in the each well was 14% to promote dissolution of the inhibitors. Within the linear range of the plot of substrate hydrolysis versus time, the reaction was quenched by trifluoroacetic acid (TFA) to a final concentration of 0.3% in each well. The activity was obtained by observing the end point absorbance reading after quenching. The percentage of inhibition was calculated by dividing the absorbance measured in the presence of inhibitor plus enzyme (inhibited signal) by the absorbance measured in the presence of enzyme alone (full signal) minus the absorbance obtained in the absence of both inhibitors and the enzyme (background).

High-throughput Cruzain Assay:

Cruzain protein has been expressed in bacteria as an inactive, insoluble fusion protein that is easily isolated from the bacterial lysate. The inactive enzyme has been successfully refolded and processed to yield an active form (Eakin et al., *J. Biol. Chem.*, 267:7411–7420, 1992). This recombinant enzyme (Eakin et al., *J. Biol. Chem.*, 268:6115–6118, 1993) was used in the following assay. The recombinant enzyme used in these experiments was provided by Dr. Charles Kraik (University of California, San Francisco).

A stock solution of cruzain was prepared, having a concentration of 435 μM in 20 mM Bis-Tris, pH 5.8. A fluorometric high throughput cruzain assay similar in concept to the cathepsin B assay described above was developed. The same substrate, Z—F—R—AMC, was also used in the cruzain assay ($K_m$=1.0 μM). The assay conditions were the same as in the cathepsin B assay except as noted below. The substrate concentration in the assay was 3 μM, and the assay buffer was composed of 50 mM sodium acetate containing 5 mM EDTA, pH 5.5.

In each well, the reaction was activated by the addition of cruzain (final concentration, 0.4 nM) that had been previously activated by incubating with 5 mM dithiothreitol at 4° C. The final assay concentration of the compound was noted. The final concentration of DMSO was 10%. The reaction was quenched by the addition of 100 nM of the irreversible cruzain inhibitor E-64 (Boehringer Mannheim, Indianapolis, Ind.) dissolved in 1:1 water:ethanol. The assay was carried out at room temperature (22° C.). All reagent stocks were left at 22° C., except the cruzain stock was kept at 4° C.

Other high-throughput assays were performed using thrombin (such testing can be performed, e.g., according to the method described in Balasubramian et al., *J. Med. Chem.*, 36:300–303 (1993)), factor Xa (such testing can be performed, e.g., according to the method described in Rezaie et al. *J. Biological Chem.*, 270(27): 16176–16181 (1995)) and 92 kDa gelatinase (such testing can be performed, e.g., according to the method described in Knight et al., *FEBS Lett.*, 296:263–266 (1992)) as targets.

Example 5

A chemical set of approximately 168,000 low molecular weight organic compounds was assayed for inhibitory activity against cathepsin B, cruzain, thrombin, factor Xa, and 92 kDa gelatinase using the assays described in Example 4. The 168,000 compounds were representative of 33 arrays each based on a different molecular core structure, and included 38,000 α-ketoamide derivatives and 130,000 non-α-ketoamides.

FIG. 3 summarizes the number and percentage (i.e., "hit rate") of compounds in each array that produced greater than 75% inhibition at a 10 μM compound concentration. As shown in FIG. 3, the hit rates for the 38,000 α-ketoamides against the cysteine proteases (i.e., cruzain and cathepsin B) were significantly higher than those observed for the same compounds against the serine proteases (i.e., thrombin and factor Xa) or the metalloprotease (i.e., 92 kDa gelatinase). A similar difference in hit rate did not exist for the 130,000 other compounds. Specifically, FIG. 3 shows that the hit rate for the α-ketoamides against cathepsin B was 27 times higher than the hit rate for the other compounds against cathepsin B (0.754% v. 0.0273%). For cruzain, the α-ketoamide hit rate was 3.2 times higher (8.33% v. 2.60%). Three specific arrays of α-ketoamides (i.e., α-ketoamide-AMO, α-ketoamide-triazine, and α-ketoamide-thiourea), in particular, demonstrated higher hit rates as compared to the 130,000 other compounds; the hit rates were 1.83, 16.5, and 2.2 times higher for cathepsin B, and 3.4, 11.5, and 3.68 times higher for cruzain, respectively.

Example 6

Of all of the α-ketoamide derivatives studied (see Example 5), the thiourea conjugated compounds (FIG. 1B)

demonstrated the greatest potency towards cruzain, and the greatest selectivity over other proteases. 307 of the 3200 compounds in the α-ketoamide-thiourea array (more than 9%) exhibited greater than 75% inhibition at 10 μM, as compared to 2 compounds with greater than 75% inhibition of cathepsin B and 0 compounds for 92 kDa gelatinase (FIG. 3).

The 307 α-ketoamide-thioureas that produced greater than 75% inhibition of cruzain were re-tested in quadruplicate at 1 μM, and six compounds were identified that produced more than 50% inhibition. Based on the structures of these compounds, and on synthetic feasibility considerations, four of these six, and two additional, structurally related compounds, were resynthesized. The six resulting compounds are shown in FIG. 4 (compounds 1–6).

To test the potency and specificity of compounds 1–6, they were tested in triplicate in the in vitro enzyme inhibition assays described in Example 4 at dosages ranging from 10 nM to 50 μM. The percentage of inhibition was plotted against the logarithm of inhibitor concentration, and the inhibitor concentration at 50% inhibition was determined (IC$_{50}$). Compounds 1–6 in FIG. 4 all demonstrated single digit micromolar potency or better against cruzain; compounds 4 and 5 were the most potent, with IC$_{50}$ values of 70 and 80 mM, respectively (see FIG. 4). Compound 4 demonstrated the greatest selectivity over cathepsin B (i.e., greater than 20-fold).

Compounds 1–6 also displayed selectivity over five serine and metalloproteases as shown in FIG. 5. FIG. 5 lists the percentage inhibition measured in quadruplicate from in vitro assays for activity against thrombin, trypsin, plasmin, 92 kDa gelatinase (92 K), and tumor necrosis factor alpha converting enzyme (TACE), as well as cruzain. No significant inhibitory activity was noted against the serine and metalloproteases as compared with cruzain.

These data show that the α-ketoamide-based compounds are generally more potent inhibitors against cysteine proteases than against other protease classes. The data also show that certain α-ketoamide thiourea-based compounds are potent and specific inhibitors of cruzain. The discovery of these inhibitors was accelerated by the integration of high throughput testing and synthesis methods, and the logically ordered, spatially addressable nature of the array (see, e.g., FIG. 6).

Figure 6:
FIG. 6 is a table illustrating the activity pattern that results when a logically ordered, spatially arranged array is screened for biological activity.

FIG. 6 shows primary screening results for the α-ketoamide thiourea array at 10 μM concentration against cruzain. Array locations corresponding to compounds with inhibition greater than 75% are darkened. FIG. 6 illustrates the pattern of activity that results when a logically ordered, spatially arranged array is screened for biological activity. The activity pattern facilitates understanding of the structure-activity relationship between the compounds and the target.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for preparing a mono α-ketoamide of a diamine compound, the method comprising:

reacting a diamine with an α-ketoester compound, under conditions such that a monoacylated diamine is prepared, wherein the diamine comprises the structure B—NH—Y—NH—C, wherein Y is ethylbenzene-2',4-diyl or toluene-1',4-diyl, and B and C are each independently selected from the group consisting of hydrogen, alkyl groups, carbocyclic groups, and aryl groups.

2. The method of claim 1, wherein the α-ketoester compound is represented by the structure:

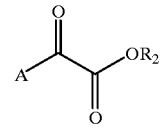

wherein A and R$_2$ are each independently selected from the group consisting of alkyl groups, carbocyclic groups, and aryl groups.

3. The method of claim 2, wherein A is selected from the group consisting of 3-trifluoromethylphenyl, phenyl, 4-bromophenyl, 2,4-difluorophenyl, 4-nitrophenyl, 4-tert-butylphenyl, 3-tolyl, 3-methoxyphenyl, 3-fluorophenyl, and 4-methoxyphenyl.

4. The method of claim 2, wherein A is 2-benzothienyl.

5. The method of claim 2, wherein A is p-biphenyl.

6. The method of claim 2, wherein R$_2$ is an alkyl group.

7. The method of claim 2, wherein R$_2$ is a methyl.

8. The method of claim 1, wherein B and C are identical to each other.

9. The method of claim 1, wherein B and C are both hydrogen.

10. The method of claim 1, wherein the reacting step comprises reacting the diamine with the α-ketoester compound in a solvent.

11. The method of claim 10, wherein the solvent is methanol.

* * * * *